(12) United States Patent
Jang

(10) Patent No.: US 6,264,632 B1
(45) Date of Patent: *Jul. 24, 2001

(54) CATHETER SYSTEM HAVING A BALLOON ANGIOPLASTY DEVICE DISPOSED OVER A WORK ELEMENT LUMEN

(75) Inventor: Yue-Teh Jang, Fremont, CA (US)

(73) Assignee: Cardiovascular Imaging Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/379,930

(22) Filed: Aug. 23, 1999

Related U.S. Application Data

(63) Continuation of application No. 08/861,397, filed on May 21, 1997, now Pat. No. 5,941,870, which is a continuation of application No. 08/504,363, filed on Jul. 19, 1995, now abandoned, which is a continuation of application No. 08/291,215, filed on Aug. 16, 1994, now abandoned, which is a continuation of application No. 08/100,642, filed on Jul. 30, 1993, now Pat. No. 5,364,347, which is a continuation of application No. 07/975,752, filed on Nov. 13, 1992, now abandoned.

(51) Int. Cl.$^7$ ............................................. A61M 29/00
(52) U.S. Cl. ............................................. 604/97.01
(58) Field of Search ............................. 606/191, 192, 606/194; 604/500, 507–510, 96.01, 104, 523, 97.01

(56) References Cited

U.S. PATENT DOCUMENTS 5,219,335 * 6/1993 Willard et al. .................. 604/164

* cited by examiner

Primary Examiner—Anhtuan T. Nguyen
(74) Attorney, Agent, or Firm—Lyon & Lyon LLP

(57) ABSTRACT

An intravascular catheter system has a balloon angioplasty device disposed about a common lumen near its distal end. The common lumen is in communication with multiple lumens within a proximal region of the catheter body to allow for positioning of the catheter over a movable guide wire and convenient delivery of imaging or interventional devices to a desired region of the blood vessel being treated.

10 Claims, 2 Drawing Sheets

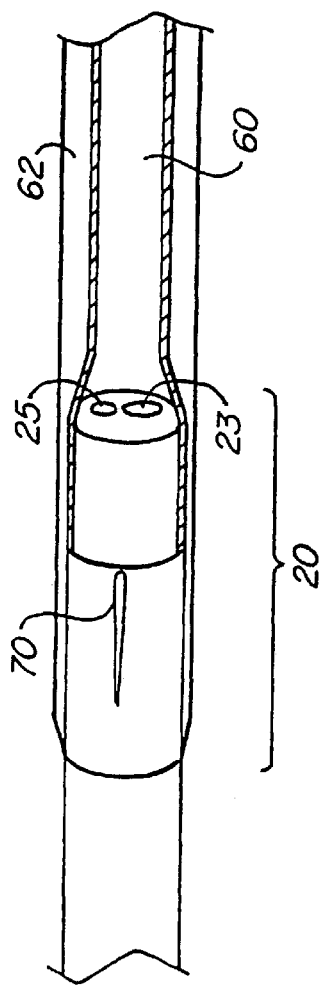
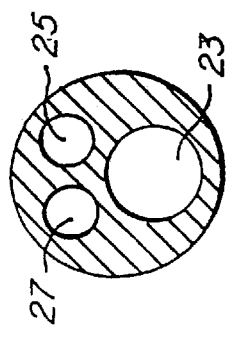
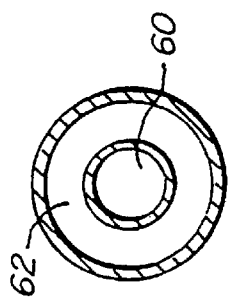
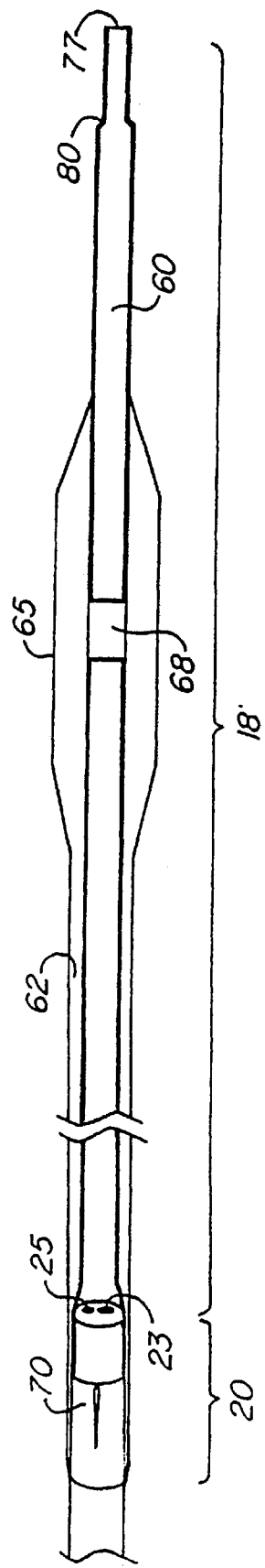

CATHETER SYSTEM HAVING A BALLOON ANGIOPLASTY DEVICE DISPOSED OVER A WORK ELEMENT LUMEN

This is a continuation of application Ser. No. 08/861,397, filed May 21, 1997, now issued as U.S. Pat. No. 5,941,870, which is a continuation of Ser. No. 08/504,363, filed Jul. 19, 1995 now abandoned, which is a continuation of Ser. No. 08/291,215, filed Aug. 16, 1994 now abandoned, which is a continuation of Ser. No. 08/100,642, filed Jul. 30, 1993 now issued as U.S. Pat. No. 5,364,347, which is a continuation of Ser. No. 07/975,752, filed Nov. 13, 1992, now abandoned.

The present application is related to application Ser. No. 07/930,977, filed Aug. 14, 1992, now U.S. Pat. No. 5,203,338, Ser. No. 07/975,769, filed Nov. 13, 1992, now U.S. Pat. No. 5,997,523; and Ser. No. 07/976,228, filed Nov. 13, 1992, now U.S. Pat. No. 5,314,408, the full disclosures of which are incorporated herein by reference.

BACKGROUND OF THE INVENTION

1. Field of the Invention

The present invention relates generally to catheter systems for imaging and treatment of stenoses within a patient's vascular system and more particularly to a catheter system in which a balloon angioplasty device can be delivered along with an imaging or interventional work element to a desired region within a blood vessel.

2. Description of the Background Art

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed limbs of the body and coronary blood vessels that feed the heart. Localized accumulation of deposits within regions of the blood vessels may result in stenosis, or narrowing of the vascular channel. When this occurs, blood flow is restricted and the person's health is at serious risk.

Numerous approaches for reducing and removing such vascular deposits have been proposed, including balloon angioplasty, in which a balloon-tipped catheter is used to dilate a stenosed region within the blood vessel; atherectomy, in which a blade or other cutting element is used to sever and remove the stenotic material; laser angioplasty, in which laser energy is used to ablate at least a portion of the stenotic material; and the like.

In order to apply such intervention techniques more effectively, a variety of vascular imaging devices and methods may be employed. Of particular interest to the present invention, imaging catheters having ultrasonic transducers at their distal ends have been employed to produce images of the stenotic region from within the blood vessel.

A number of specific designs for ultrasonic imaging catheters have been described. An early design is illustrated in U.S. Pat. No. 4,794,931, where the mechanical components of the imaging system are located within a housing at the distal end of the catheter. The housing includes a fixed guidewire, which is used to position the catheter within the vascular system, at its distal tip. While the use of such fixed-guidewire designs can provide excellent image quality, under some circumstances it is desirable to use an "over-the-wire" design where the catheter may be introduced over a separate (movable) guidewire. The use of a movable guidewire offers certain advantages, including improved steering capability through narrow regions and easier catheter exchange, e.g., substitution of an interventional catheter for the imaging catheter.

Exchanging the imaging catheter for an interventional or other catheter within a patient's vascular system is time consuming and may be injurious to the patient. It is desirable therefore to combine imaging and interventional capabilities in a single catheter system. A design for an ultrasonic imaging catheter having a balloon angioplasty device is described in U.S. Pat. No. 5,117,831. One depicted embodiment uses a fixed guidewire and is thus subject to the disadvantages noted above. Another embodiment has a guidewire movable through the ultrasonic imaging transducer and its associated drive shaft. This requires that the transducer and the drive shaft be made hollow and increased in diameter in order to accommodate the guidewire therein. Additionally, the transducer is fixed at the end of the drive shaft and not movable along the length of the catheter.

To be able to cross very narrow lesions, the diameter of the catheter should be as small as possible at its distal end. Furthermore, the need to move the catheter body within the patient should be minimized. The blood vessel interior is delicate, may be weakened by disease, and is therefore susceptible to injury from movement of the catheter body within it.

For the reasons stated above, it would be advantageous to provide a catheter capable of delivering a balloon angioplasty system in combination with an imaging or interventional work element to a region of interest within the vascular system. Such delivery should be accomplished with a minimum repositioning of the catheter body within the blood vessel. Additionally, the catheter should be as narrow as possible at its distal end to allow for entry into and through narrow and tortuous regions of the patient's vascular system.

SUMMARY OF THE INVENTION

The present invention provides a catheter system having the ability to deliver both an angioplasty balloon and another work element for imaging or treating a region within a patient's vascular system. The catheter system comprises a catheter body having at least a proximal and a distal region. The proximal region has at least two lumens, one for carrying a movable guidewire and another for carrying a work element. The work element will typically be an ultrasonic imaging transducer but may be another imaging device or even an interventional device for treating the blood vessel in combination with the angioplasty balloon. The distal region of the catheter body has a common lumen connected to and in communication with the two lumens of the proximal region. The angioplasty balloon is disposed about the common lumen of the distal region, and the catheter system further includes an associated means for inflating the balloon, typically an inflation lumen extending from the proximal end of the catheter body to the balloon.

The catheter of the present invention will allow for the performance of rapid and convenient balloon angioplasty and imaging or other treatment of the diseased vessel while minimizing the need to reposition the catheter body between procedures. Additionally, the distal end of the catheter will be relatively narrow to allow for movement of the catheter into restricted spaces of the patient's vascular system and particularly into narrow regions and stenoses within the coronary arteries.

BRIEF DESCRIPTION OF THE DRAWINGS

FIG. 2A is a cross-sectional view through section line A—A of the catheter depicted in FIG. 1;

FIG. 2B is a cross-sectional view through section line B—B of the catheter depicted in FIG. 1;

FIG. 3 depicts a transition region between proximal and distal regions of the body of the catheter depicted in FIG. 1; and FIG. 4 depicts the transition region and distal region of an alternate preferred embodiment of a catheter according to the present invention.

DESCRIPTION OF SPECIFIC EMBODIMENTS

Figure 1:
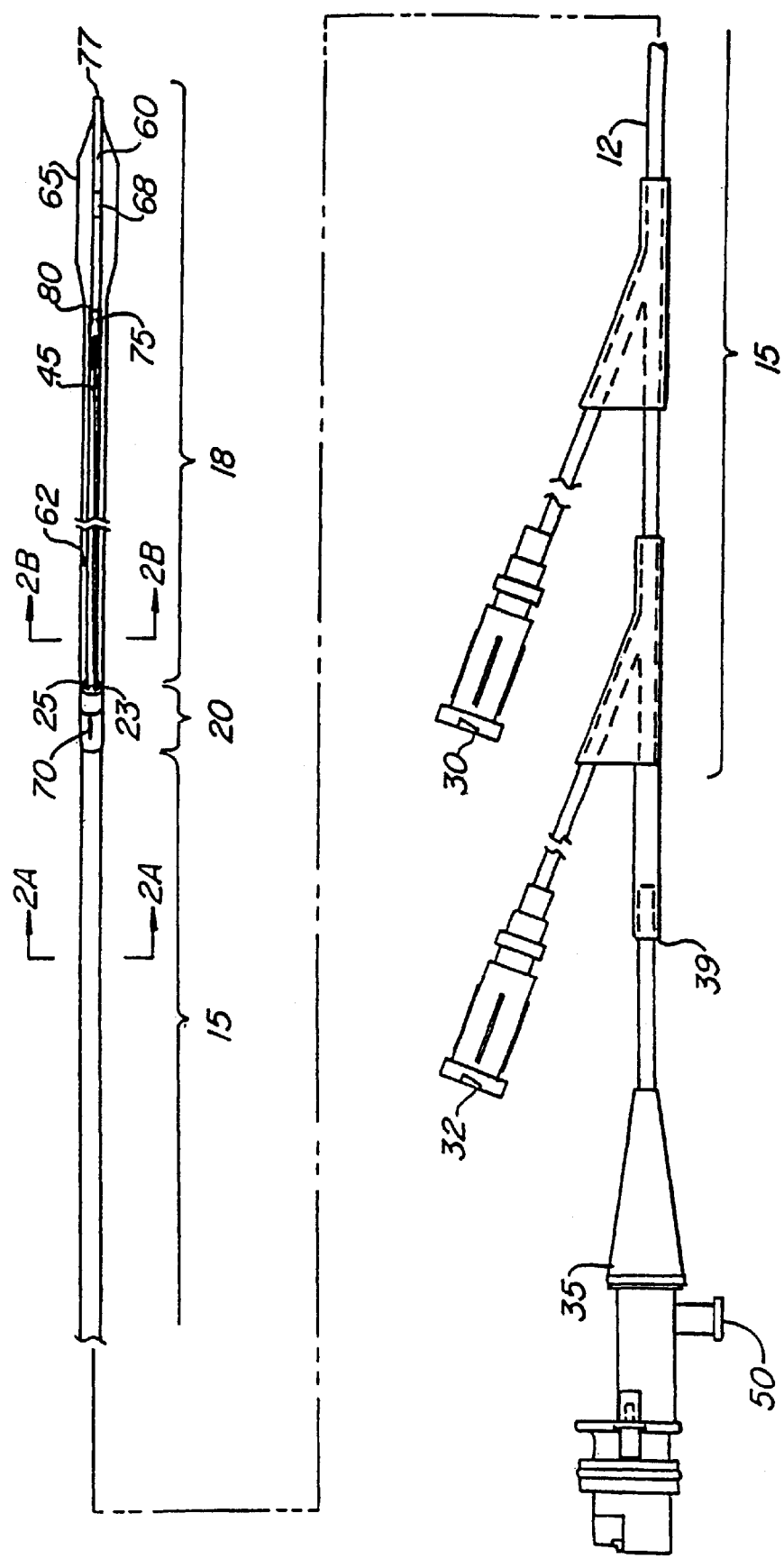
FIG. 1 depicts a preferred embodiment of a catheter according to the present invention.

A catheter according to the present invention will comprise an elongate catheter body having proximal and distal ends and at least two regions, a proximal region and a distal region. The proximal region of the catheter body will have at least two lumens extending at least partly therethrough. The distal region of the catheter body will have a single common lumen in communication with both of the lumens of the proximal region. Additionally, an inflatable angioplasty balloon will be disposed about the common lumen of the distal region of the catheter.

In use, a catheter according to the present invention will be advanced over a guidewire into a patient's vascular system. First, the guidewire will be advanced alone into the patient until the guidewire lies within a particular region of interest. This will typically be a region in which a blood vessel has been narrowed by a stenotic lesion. The distal end of the guidewire will be advanced into the region of stenosis with the proximal end of the guidewire remaining outside of the patient's body.

The proximal end of the guidewire may then be inserted into the distal end of the catheter body and fed through the common lumen of the distal region. When the proximal end of the guidewire reaches a transition region between the distal and proximal regions of the catheter body, the guidewire will be directed into a particular guidewire lumen of the proximal region.

Once the guidewire has been directed into the guidewire lumen, the catheter will be advanced into the patient's vascular system until the common lumen of the distal region lies within the region of interest. During advancement of the catheter into the blood vessel, the proximal end of the guidewire will exit the catheter body through a guidewire port located some distance proximal of the distal region (in either an "over-the wire" configuration, or a "monorail" configuration). The proximal end of the guidewire may then be grasped and pulled back sufficiently to withdraw the distal end of the guidewire into the guidewire lumen and clear of the common lumen of the distal region. An ultrasonic imaging transducer or other work element may then be advanced through another lumen of the proximal region and into the common lumen for imaging the region of interest.

Prior to inflation of the balloon, the imaging element will normally be withdrawn from the common lumen into its lumen in the proximal region. The guidewire will then be readvanced through the common lumen and into the blood vessel.

At present, it is highly advantageous for the guidewire to be in place in the common lumen when the balloon is inflated. When the balloon is inflated, blood flow through the blood vessel will be blocked by the balloon. An adverse ischemic condition may result and rapid removal of the catheter from the blood vessel may be required. If the guidewire is in position in the common lumen, rapid catheter removal will be made easier. Additionally, replacement of the catheter over the guidewire will be more convenient once the ischemic condition has abated.

After the initial balloon inflation, successive steps of imaging and dilation may be repeated as desired. Alternatively, some other form of interventional device, for example a mechanical cutter or laser ablation device, may be advanced through the distal tip of the catheter body.

Thus, a catheter according to the present invention will allow for the convenient delivery of a balloon angioplasty device in combination with another interventional or imaging device to a region of interest within the patient. Because the catheter uses a single common distal lumen, it may be made with a reduced profile at its distal end. This will allow delivery of the balloon angioplasty, imaging, or other interventional devices even within narrow, tortuous regions of the patient's vascular system. Furthermore, the various work elements are delivered through a common lumen lying within the balloon, thus minimizing the need to reposition the catheter body between treatment steps.

FIG. 1 depicts a preferred embodiment of a catheter according to the present invention. The catheter has a catheter body 12, which comprises proximal region 15, distal region 18, and transition region 20. FIG. 2A is a cross-sectional view of the proximal region of catheter body 12 through section line A—A. In this embodiment, proximal region 15 has three lumens, work element lumen 23, guidewire lumen 25, and proximal balloon inflation lumen 27. Other embodiments could have still more lumens to accommodate additional imaging or interventional devices, as described generally in co-pending U.S. patent application Ser. No. 07/975,769, filed on the same day as the present application, the full disclosure of which is incorporated herein by reference. Guidewire port 30 and balloon inflation port 32 (FIG. 1) place guidewire lumen 25 and proximal balloon inflation lumen 27 in communication with the exterior of the catheter near its proximal end.

In the embodiment depicted in FIG. 1, drive shaft 45 is reciprocatably disposed within work element lumen 23. (For clarity, only a distal portion of drive shaft 45 is illustrated.) At its proximal end, work element lumen 23 is in communication with expandable member 39, which is connected in turn to proximal housing 35. The proximal housing is adapted to connect a proximal end of drive shaft 45 to a drive motor (not shown) for rotating the drive shaft.

Expandable member 39 allows the drive shaft to be conveniently advanced and retracted within work element lumen 23 by moving proximal housing 35 with respect to the catheter body to lengthen or shorten expandable member 39 as desired. Proximal housing 35 is provided further with flush port 50, to allow for the flushing of trapped air bubbles from within work element lumen 23. The construction and use of proximal housing 35 in conjunction with a multilumen catheter is more fully described in co-pending U.S. patent application Ser. No. 07/976,228, filed the same day as the present application, the full disclosure of which is incorporated herein by reference.

A cross-section through distal region 18 of catheter body 12 through section line B—B is depicted in FIG. 2B. As can be seen therein, distal region 18 has two concentric lumens. In the distal region, common lumen 60 is disposed within distal balloon inflation lumen 62.

Referring again to FIG. 1, balloon 65 is disposed about common lumen 60. The balloon is in communication with distal balloon inflation lumen 62 to provide for inflation of the balloon. Radiopaque band 68 is wrapped around the common lumen at a position within the balloon to allow for fluoroscopic imaging to assist in placing the balloon within the desired region of the blood vessel.

The length of common lumen 60 will generally be between 5 and 30 centimeters, with balloon 65 typically having a length in the range of 1.5–4.5 centimeters. The balloon crossing profile, the minimum width crossable by the balloon when deflated, will typically be in the range of 0.020–0.045 inches. The outside diameter of the balloon when inflated within a blood vessel will commonly be between 1.5 and 4.5 millimeters. The foregoing ranges are set forth solely for the purpose of illustrating typical device dimensions. The actual dimensions of a device constructed according to the principles of the present invention may obviously vary outside of the listed ranges without departing from those basic principles.

FIG. 3 depicts transition region 20 between the three parallel lumens of proximal region 15 and the two concentric lumens of distal region 18. Transition region 20 provides for communication between common lumen 60 of the distal region and both guidewire lumen 25 and work element lumen 23 of the proximal region. Also, distal balloon inflation lumen 62 is placed in communication with proximal balloon inflation lumen 27 through balloon inflation lumen connection 70, which is formed by cutting through the exterior of proximal region 15 to expose a portion of the proximal balloon inflation lumen and sealing the end of the balloon inflation lumen to close it off from common lumen 60. Thus, a continuous inflation path exists from balloon inflation port 32, through proximal and distal balloon inflation lumens 27 and 62, and into balloon 65. Injection of fluid into balloon inflation port 32 will thereby result in inflation of balloon 65.

It is contemplated that the catheter depicted in FIG. 1 will be used as follows. First, a conventional guidewire will be advanced into the patient's vascular system until it lies within the region of stenosis. Next, the guidewire will be inserted into distal tip 77 (FIG. 1) of the catheter and through common lumen 60 of distal region 18. The catheter will then be advanced into the patient's body over the guidewire until the guidewire reaches transition region 20. At this point, the guidewire will be directed into guidewire lumen 25 and through the proximal region until it exits the catheter through guidewire port 30 as the catheter is advanced further into the patient's body. Eventually, the catheter will be advanced to a point where common lumen 60 and balloon 65 both lie within the region of interest.

The operator of the system can then grasp the guidewire at the end protruding from the guidewire port. The operator will pull the guidewire back a short distance into guidewire lumen 25 of proximal region 15 in order to clear common lumen 60 of distal region 18. A work element 75, which will typically be an ultrasonic imaging transducer, fixed to the distal end of drive shaft 45, may then be advanced through work element lumen 23 of the proximal region and into the common lumen of the distal region. Imaging of the region of interest may then take place.

Following imaging, work element 75 will be retracted into its lumen in the proximal region. The guidewire will be readvanced through the common lumen into the blood vessel. Balloon 65 may then be inflated to dilate the region of interest and thereby reduce the stenosis therein. Successive steps of imaging, guidewire replacement, and treatment may be repeated as desired until the stenosis has been satisfactorily reduced. If complications result due to restriction by the balloon of blood flow through the vessel, the catheter may be quickly and conveniently pulled back over the guidewire to restore blood flow through the vessel.

FIG. 1 depicts a catheter in which the common lumen is narrowed at a restriction 80 just proximal to the balloon. Distal of the restriction, the common lumen will be just large enough to allow passage of the guide wire. This allows the balloon crossing profile, the width of the catheter in the region of the balloon when not inflated, to be as small as possible. This is advantageous in that it allows the balloon to be advanced into narrow and tortuous regions of the blood vessel. Placing the restriction proximal to the balloon is disadvantageous however, in that it may prevent entry of the work element into the common lumen within the balloon. Thus, some repositioning of the catheter body within the blood vessel, i.e., advancement of the catheter body a further into the blood vessel, may be necessary to allow for imaging of the treated region.

FIG. 4 depicts the distal region of an alternative preferred embodiment in which the common lumen is not restricted in the region proximal to the balloon. In this embodiment, the work element may travel through the common lumen into, through and beyond the balloon. This is advantageous in that it allows for imaging of the blood vessel throughout the region of the balloon without repositioning the catheter body.

As discussed above, it is desirable at present to have the guidewire in place within the common lumen during balloon inflation in case rapid withdrawal of the catheter over the guidewire becomes necessary. However, future developments in interventional devices and techniques may make this unneccesary. If this becomes the case, imaging will be possible from within the balloon even while the balloon is being inflated. Of course an increased diameter common lumen within the balloon requires a slightly larger balloon crossing profile. Some ability to enter narrow regions must thereby be sacrificed in order to achieve a more flexible imaging capability.

The embodiment of FIG. 4 depicts the common lumen having restriction 80 at some distance distal to balloon 65. This restriction will prevent the accidental exit of the work element from the distal tip 77 of the catheter body while still allowing passage of the guidewire. This prevents injury to the blood vessel wall, which might result from accidental contact by the rotating work element. A catheter according to the present invention could also be made to carry an interventional work element such as a rotating cutter or a laser ablation device. In such a case, it would be necessary for the work element to advance beyond the distal tip 77 of the catheter body. In such a catheter system, restriction 80 would be omitted altogether to allow for unhindered passage of the work element.

Although the foregoing invention has been described in some detail by way of illustration and example for purposes of clarity of understanding, it will be obvious that certain changes and modifications may be practiced which will still fall within the scope of the appended claims.

What is claimed is:

1. A vascular catheter system comprising:
   a catheter body having proximal and distal ends, and a proximal and a distal region, the proximal region having at least two lumens and the distal region having a common lumen connected to and in communication with both lumens of the proximal region;
   a balloon disposed about the common lumen;
   means for inflating the balloon;
   a rotatable drive shaft having proximal and distal ends, the drive shaft reciprocatably disposed within a lumen of the proximal region of the catheter body; and
   a work element fixed to the distal end of the drive shaft, the work element positionable within the common lumen of the distal region of the catheter body.

2. The vascular catheter system of claim 1, wherein the work element is positionable within the balloon.

3. The vascular catheter system of claim 1, wherein the work element is extendable to apposition past the balloon.

4. The vascular catheter system of claim 1, wherein the work element comprises an imaging device.

5. The vascular catheter system of claim 4, wherein the imaging device comprises an ultrasonic transducer.

6. The vascular catheter system of claim 1, wherein the work element comprises an interventional device.

7. The vascular catheter system of claim 1, further comprising:

an axially expandable member connected to the proximal end of the catheter body and a proximal housing connected to the proximal end of the drive shaft and the axially expandable member, whereby the work element may be advanced from a position within a lumen of the proximal region into a position within the common lumen of the distal region by moving the proximal housing with respect to the catheter body.

8. A method for imaging and treating a region of a patient's blood vessel using a catheter system comprising a guidewire; an ultrasonic imaging transducer fixed to a distal end of a rotatable drive shaft; a catheter body having a proximal region including at least two lumens, and a distal region including a common lumen connected to and in communication with both lumens of the proximal region; and an angioplasty balloon disposed about the distal region; the method comprising the steps of:

advancing the guidewire into the blood vessel until a distal end of the guidewire lies within the stenosed region and a proximal end of the guidewire extends from the patient;

loading the proximal end of the guidewire into the common lumen of the distal region of the catheter body;

advancing the catheter body into the blood vessel until the angioplasty balloon and the common lumen lie within the region of stenosis;

inflating the balloon to dilate the blood vessel and reduce the stenosis;

retracting the distal end of the guidewire out of the common lumen into a lumen of the proximal region of the catheter body;

advancing the ultrasonic transducer and drive shaft through a lumen of the proximal region of the catheter body into the common lumen; and imaging the region of interest within the blood vessel.

9. The method of claim 8, wherein successive steps of imaging and balloon inflation are repeated as desired until the stenosis is reduced to a desired extent.

10. A method for treating a region of a patient's blood vessel using a catheter system comprising a guidewire; an interventional work element fixed to a distal end of a rotatable drive shaft; a catheter body having a proximal region including at least two lumens, and a distal region including a common lumen connected to and in communication with both lumens of the proximal region; and an angioplasty balloon disposed about the distal region; the method comprising the steps of:

advancing the guidewire into the blood vessel until a distal end of the guidewire lies within the stenosed region and a proximal end of the guidewire extends from the patient;

loading the proximal end of the guidewire into the common lumen of the distal region of the catheter body;

advancing the catheter body into the blood vessel until the angioplasty balloon and the common lumen lie within the region of stenosis;

inflating the balloon to dilate the blood vessel and reduce the stenosis;

retracting the distal end of the guidewire out of the common lumen into a lumen of the proximal region of the catheter body;

advancing the interventional work element and drive shaft through a lumen of the catheter body and through the common lumen into the blood vessel; and treating the region of interest with the interventional device.

\* \* \* \* \*

UNITED STATES PATENT AND TRADEMARK OFFICE
CERTIFICATE OF CORRECTION

PATENT NO. : 6,264,632 B1
DATED : July 24, 2001
INVENTOR(S) : Jang

It is certified that error appears in the above-identified patent and that said Letters Patent is hereby corrected as shown below:

Column 7,
Line 4, change "apposition" to -- a position --

Column 8,
Line 40, please add the following claims 11 and 12:
11. The vascular catheter system of claim 5, wherein the baloon inflation means comprises a balloon inflation lumen disposed parallel to the two lumens of the proximal region.

12. The vascular catheter system of claim 15, wherein the balloon inflation lumen lies within the catheter body at its proximal end and is disposed coaxially about the common lumen of the distal region of the catheter body.

Signed and Sealed this

Fourteenth Day of May, 2002

Attest:

*Attesting Officer*

JAMES E. ROGAN
*Director of the United States Patent and Trademark Office*